(12) United States Patent
Gross (10) Patent No.: US 6,988,986 B2
(45) Date of Patent: Jan. 24, 2006

(54) SELF-PROPELLED IMAGING SYSTEM

(75) Inventor: Yosef Gross, Moshav Mazor (IL)

(73) Assignee: G. I. View, Tel Aviv (IL)

( * ) Notice: Subject to any disclaimer, the term of this patent is extended or adjusted under 35 U.S.C. 154(b) by 0 days.

(21) Appl. No.: 10/302,897

(22) Filed: Nov. 25, 2002

(65) Prior Publication Data

US 2004/0102681 A1 May 27, 2004

(51) Int. Cl.
*A61B 1/00* (2006.01)

(52) U.S. Cl. .................. 600/114; 600/115; 600/116
(58) Field of Classification Search ......... 600/114–117, 600/109, 139, 127
See application file for complete search history.

(56) References Cited

U.S. PATENT DOCUMENTS

| | | | | | |
|---|---|---|---|---|---|
| 4,148,307 A | * | 4/1979 | Utsugi | .................. | 600/116 |
| 4,176,662 A | * | 12/1979 | Frazer | .................. | 600/114 |
| 4,690,131 A | * | 9/1987 | Lyddy et al. | ............... | 600/115 |
| 5,662,587 A | * | 9/1997 | Grundfest et al. | .......... | 600/114 |
| 5,906,591 A | * | 5/1999 | Dario et al. | ............. | 604/95.03 |
| 6,007,482 A | * | 12/1999 | Madni et al. | ............... | 600/115 |
| 6,702,735 B2 | * | 3/2004 | Kelly | .................. | 600/115 |

\* cited by examiner

*Primary Examiner*—Beverly M. Flanagan
(74) *Attorney, Agent, or Firm*—Hoffman, Wasson & Gitler

(57) ABSTRACT

An imaging system comprising an imaging device assembled on a carrier tube, and a first outwardly expandable element and a second outwardly expandable element mounted on the carrier tube, wherein the second expandable element is expandable both radially and axially, the imaging system comprising a mode of operation, wherein during expansion of the second expandable element, obstruction of the radial expansion of the second expandable element causes the axial expansion of the second expandable element to propel the carrier tube and the imaging device axially.

74 Claims, 6 Drawing Sheets

SELF-PROPELLED IMAGING SYSTEM

FIELD OF THE INVENTION

The present invention relates generally to medical imaging systems, and particularly to a self-propelled imaging system, suitable for imaging body lumens, such as the gastrointestinal (GI) tract.

BACKGROUND OF THE INVENTION

Many imaging devices are known for producing medical images of body lumens, such as the gastrointestinal (GI) tract. For example, endoscopy is widely used for observing, photographing tissue, and taking specimens from lesions and the like. In a conventional method of examining a colon using an endoscope, for example, the endoscope is typically manually inserted into the colon. In this manual technique, patients may often complain of abdominal pain and distention because the colon is extended or excessively dilated, thereby necessitating stopping the endoscopic procedure. Furthermore, it is not unusual for the colon to bleed and be accidentally perforated. Insertion of an endoscope through the sigmoid colon and into the descending colon, or through the splenic flexure, the transverse colon, the hepatic flexure or parts affected by previous operations may also be accompanied with difficulty. Because of these reasons, a colonoscopy is typically performed by a relatively few number of skilled practitioners, and the rate of patient pain and discomfort is high.

U.S. Pat. No. 5,337,732 to Grundfest et al. describes a robot for performing endoscopic procedures, which includes a plurality of segments attached to each other through an articulated joint. Actuators can move the segments together and apart and change their angular orientation to allow the robot to move in an inchworm or snake-like fashion through a cavity or lumen within a patient. Inflatable balloons around the segments inflate to brace a temporarily stationary segment against the lumen walls while other segments move. A compressed gas line attached to the back segment provides compressed gas to inflate the balloons and optionally to drive the actuators. The lead segment includes a television camera and biopsy arm or other sensors and surgical instruments.

SUMMARY OF THE INVENTION

The present invention seeks to provide an improved imaging system which is self-propelled, suitable for imaging body lumens, such as the gastrointestinal (GI) tract. The imaging system of the invention may be sterile and disposable, and may be manufactured at very low cost. The system causes virtually no pain to the patient, being of very low friction and providing maximum comfort and flexibility. The system provides excellent visibility and full movement control.

The imaging system of the present invention may comprise an imaging device assembled on a carrier tube. First and second outwardly expandable elements may be mounted on the carrier tube. The second expandable element may be expanded both radially and axially. In one mode of operation, in accordance with an embodiment of the invention, during expansion of the second expandable element, obstruction of the radial expansion of the second expandable element (such as when the second expandable element presses against the inner wall of a body lumen) causes the axial expansion of the second expandable element to propel the carrier tube and the imaging device axially, as is described more in detail hereinbelow. The imaging system may thus self-propel distally into the body lumen without any need for knowing the local diameter of the body lumen.

BRIEF DESCRIPTION OF THE DRAWINGS

The present invention will be understood and appreciated more fully from the following detailed description taken in conjunction with the drawings in which.

DETAILED DESCRIPTION OF THE PREFERRED EMBODIMENT

Figures 1A, 1B:
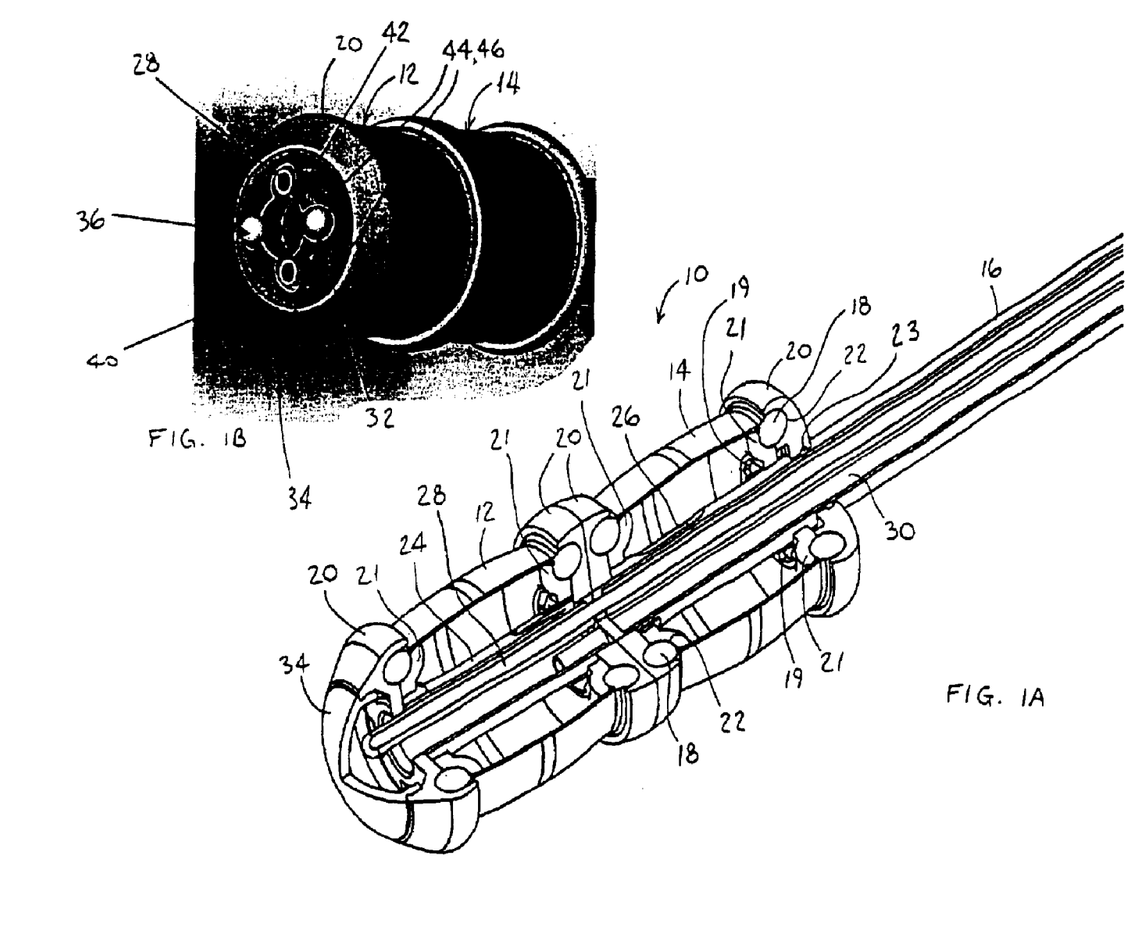
FIG. 1A is a simplified pictorial and cut-away illustration of an imaging system, constructed and operative in accordance with an embodiment of the present invention, in a contracted orientation.
FIG. 1B is a simplified pictorial illustration of a distal end of the imaging system of FIG. 1A.

Reference is now made to FIG. 1A, which illustrates an imaging system 10, constructed and operative in accordance with a preferred embodiment of the present invention.

Imaging system 10 may comprise first and second outwardly expandable elements 12 and 14. One of the outwardly expandable elements may be the proximal element and the other one may be the distal element. For example, in terms of the explanation that follows with reference to FIGS. 2–8, first element 12 is the distal element that enters the body lumen first, and second element 14 is the proximal element that enters the body lumen last.

In accordance with a preferred embodiment of the present invention, first and second expandable elements 12 and 14 expand to different shapes. First expandable element 12 may expand substantially radially with negligible axial expansion. In contrast, second expandable element 14 may expand both radially and axially, such as expanding generally spherically.

First and second expandable elements 12 and 14 may be mounted coaxially on a carrier tube 16. Carrier tube 16 may be made of any suitable, flexible, medically approved material. The expandable elements 12 and 14 may comprise full circumference or partial circumference elements.

Each expandable element 12 or 14 may comprise an inflatable, elastomeric tubular element formed with annular rings 18. Each expandable element 12 or 14 may be mounted in a pair of collar elements 20, wherein the annular rings 18 are received in annular grooves 22 formed in collar elements 20. Annular ring 18 may be held in groove 22 by means of an annular fastener 21, which snaps together with tongues 19 axially protruding from collar element 20. Collar elements 20 may be formed separately for each expandable element, and may be adjoined together by snapping together or by means of fasteners or any other suitable method. Alternatively, a single collar element 20 may be placed between first and second expandable elements 12 and 14, wherein the single collar element 20 has two sets of annular grooves 22 to receive therein the proximal annular ring 18 of the distal expandable element 12 and the distal annular ring 18 of the proximal expandable element 14. The collar elements 20 may be flexible and resilient to permit passage of imaging system 10 through folds of the GI tract. An O-ring 23 may slidingly seal the most proximal collar element 20 with respect to carrier tube 16. Accordingly, the collar elements 20 at the ends of first expandable element 12 may be fixed axially with respect to carrier tube 16, thereby preventing first expandable element 12 from expanding axially. In contrast, second expandable element 14 may slide axially relative to carrier tube 16.

In accordance with another embodiment of the invention, whether or not the collar elements 20 are fixed axially with respect to carrier tube 16 may be selectable. In this manner, a user may select which of the expandable elements may expand only radially and which may expand both radially and axially. For example, first expandable element 12 may expand both radially and axially, if desired, instead of second expandable element 14, which may cause imaging system 10 to move in a proximal direction instead of a distal direction.

Carrier tube 16 may be formed with a distal aperture 24 and a proximal aperture 26. A first supply tube 28 may be introduced through carrier tube 16 in fluid communication with distal aperture 24. Similarly, a second supply tube 30 may be introduced through carrier tube 16 in fluid communication with proximal aperture 26. First expandable element 12 may be expanded outwards by introducing therein a fluid, such as but not limited to, air or water, by means of first supply tube 28 via distal aperture 24. Likewise, second expandable element 14 may be expanded outwards by introducing therein a fluid (which may or may not be the same fluid used to expand first expandable element 12), by means of second supply tube 30 via proximal aperture 26.

Figures 1C, 1D, 1E, 1F, 1G:
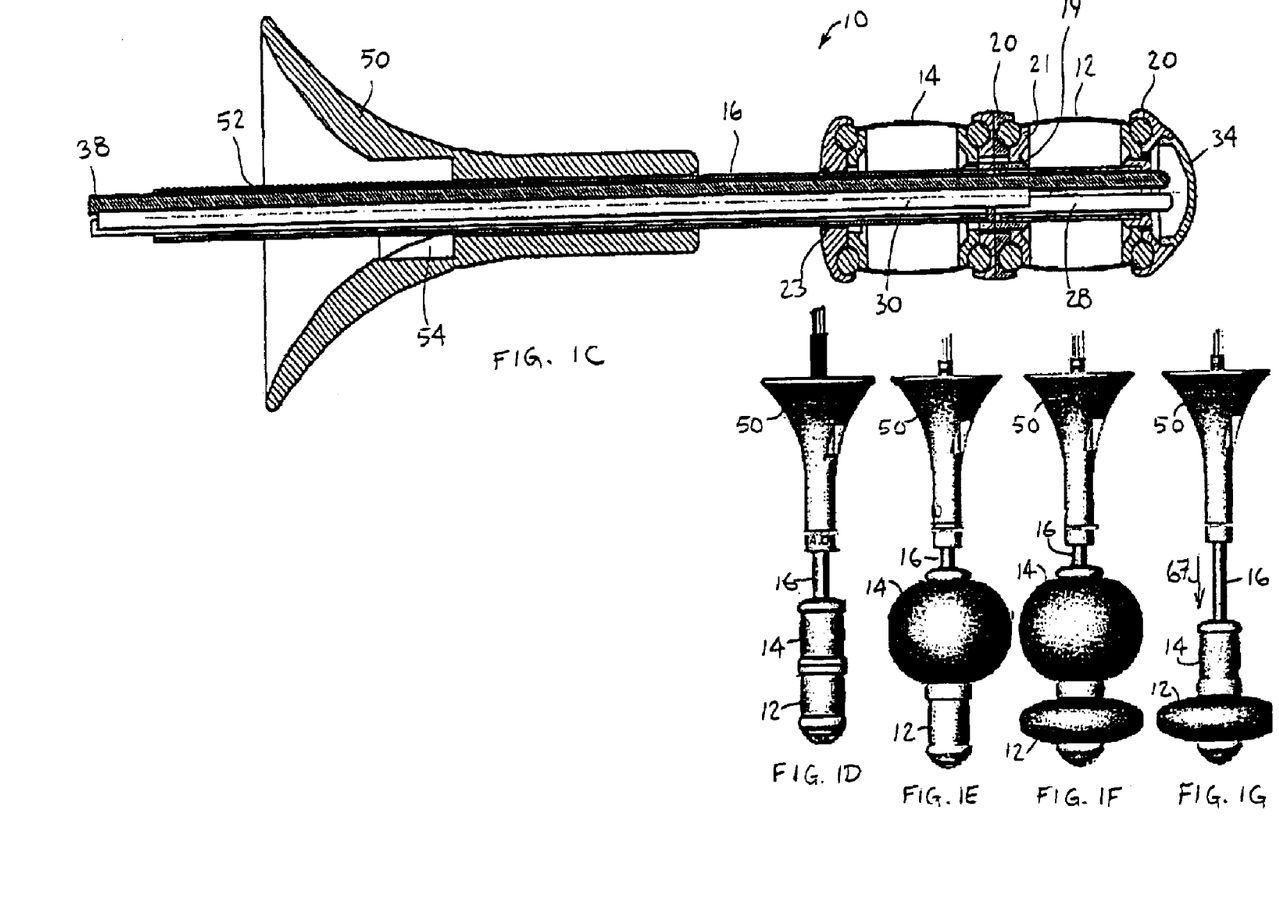
FIG. 1C is a simplified sectional illustration of the imaging system of FIG. 1A.
FIGS. 1D–1G are simplified pictorial illustrations of the imaging system of FIG. 1A, showing four steps of a mode of operation thereof, wherein in FIG. 1D a proximal expandable element and a distal expandable element are both contracted, in FIG. 1E the proximal expandable element expands generally spherically, in FIG. 1F the distal and proximal expandable elements are both expanded, and in FIG. 1G the distal expandable element is expanded while the proximal expandable element is contracted.

Reference is now made to FIGS. 1B and 1C. An imaging device 32, such as but not limited to, a CCD (charge coupled device) or CMOS (complementary metal oxide semiconductor) camera, may be mounted at a distal end of imaging system 10. For example, imaging device 32 may be mounted in the most distal collar element 20, which may be formed with a viewing window 34 through which images may be captured. Imaging device 32 and viewing window 34 may be oriented for capturing images either axially or radially with respect to carrier tube 16. A light source 36 may be provided for imaging device 18, wherein electrical wiring and/or optic fibers 38 (FIG. 1C) may be fed through carrier tube 16 to imaging device 32 and light source 36.

Imaging device 32 may be connected to an imaging processor (not shown) by optical fibers. A control system (not shown) may be provided that oversees and controls the expansion/contraction of the expandable elements 12 and 14, and other functions of imaging system 10, such as but not limited to, the timing and amount of the expansion/contraction of the expandable elements 12 and 14.

Other tubes or passageways may be provided for other functionalities. For example, a suction tube 40 (FIG. 1B) may be provided for sucking debris or other material. A tool lumen 42 may be provided for introducing therethrough mechanical devices and/or sensors (not shown), such as but not limited to, cutting devices for cutting and collecting materials for biopsies and the like, and biosensors. Additionally, passageways 44 may be provided for passing therethrough control wires 46 for directing the imaging system 10 through tight bends and the like.

A guide member 50 (FIG. 1C) may be disposed at the proximal end of carrier tube 16. Guide member 50 may be funnel-shaped, for example, for comfortable placement in a rectum of a patient (not shown). A linear encoder 52 may be disposed at the proximal end of carrier tube 16 and pass through guide member 50. Linear encoder 52 may comprise markings and the like detectable by a decoder 54 mounted on guide member 50. Decoder 54 may sense linear movement of carrier tube 16 with respect to linear encoder 52, which movement is described in greater detail hereinbelow.

It is noted that the electrical and optical components may be self-contained in imaging system 10, so that the entire system 10 is fully independent of external wiring. In such an embodiment, imaging system 10 may wirelessly transmit or receive data to or from an external processor (not shown).

Reference is now made to FIGS. 1D–1G and FIGS. 2–5, which illustrate imaging system 10 in different orientations for self-propulsion through a body lumen 60, such as but not limited to, the colon, in accordance with an embodiment of the present invention. (The body lumen 60 is omitted in FIGS. 1D–1G for clarity.)

Figure 2:
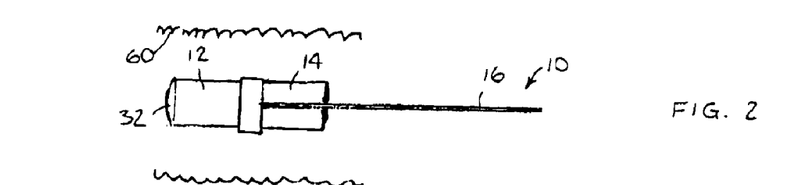
FIG. 2 is a simplified side-view illustration of the imaging system of FIG. 1A inserted in a body lumen in a contracted orientation, prior to self-propulsion therethrough, in accordance with an embodiment of the present invention.
Figure 3:
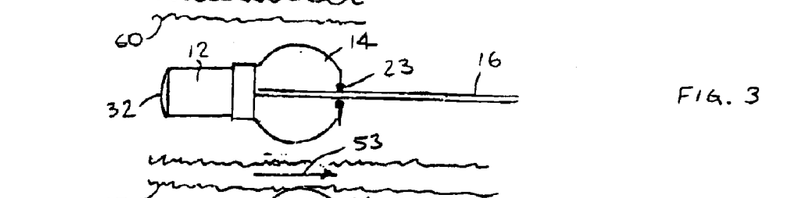
FIG. 3 is a simplified side-view illustration of the imaging system of FIG. 1A with the proximal expandable element partially expanded and not yet touching the inner wall of the body lumen.

In the initial orientation of FIGS. 1D and 2, none of the expandable elements 12 and 14 are expanded, as in FIG. 1A. In this contracted orientation, imaging system 10 may be inserted in body lumen 60. In FIG. 3, second (proximal) expandable element 14 may be expanded outwardly. As seen in FIG. 3, before the proximal expandable element 14 touches the inner wall of body lumen 60, it may expand both radially and axially (e.g., spherically). O-ring 23 slides proximally along carrier tube 16, as indicated by arrow 53, with the result that carrier tube 16 (along with imaging device 32) does not yet advance in body lumen 60.

Figure 4:
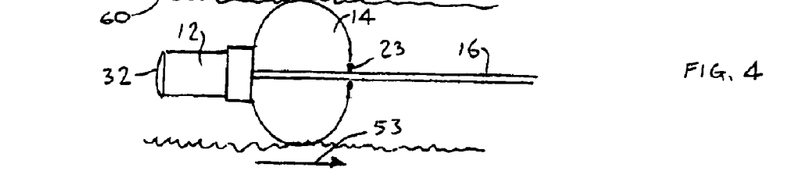
FIG. 4 is a simplified side-view illustration of the imaging system of FIG. 1A with the proximal expandable element further expanded and touching the inner wall of the body lumen.

In FIG. 4, the proximal expandable element 14 has expanded sufficiently so that it touches the inner wall of body lumen 60. Carrier tube 16 (along with imaging device 32) has still not advanced in body lumen 60, and O-ring 23 has continued to slide proximally along carrier tube 16, as indicated by arrow 53. The orientation of FIG. 4 is shown in pictorially in FIG. 6.

Figure 5:
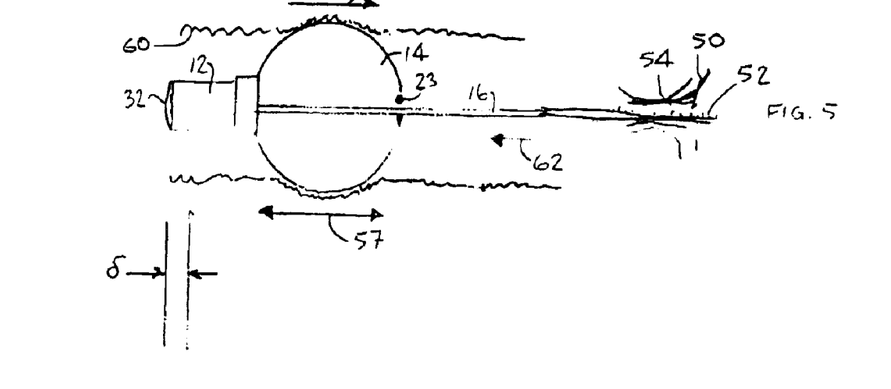
FIG. 5 is a simplified side-view illustration of the imaging system of FIG. 1A with the proximal expandable element further expanded, pressing against the inner wall of the body lumen, and propelling the imaging system distally through the body lumen.
Figure 6:
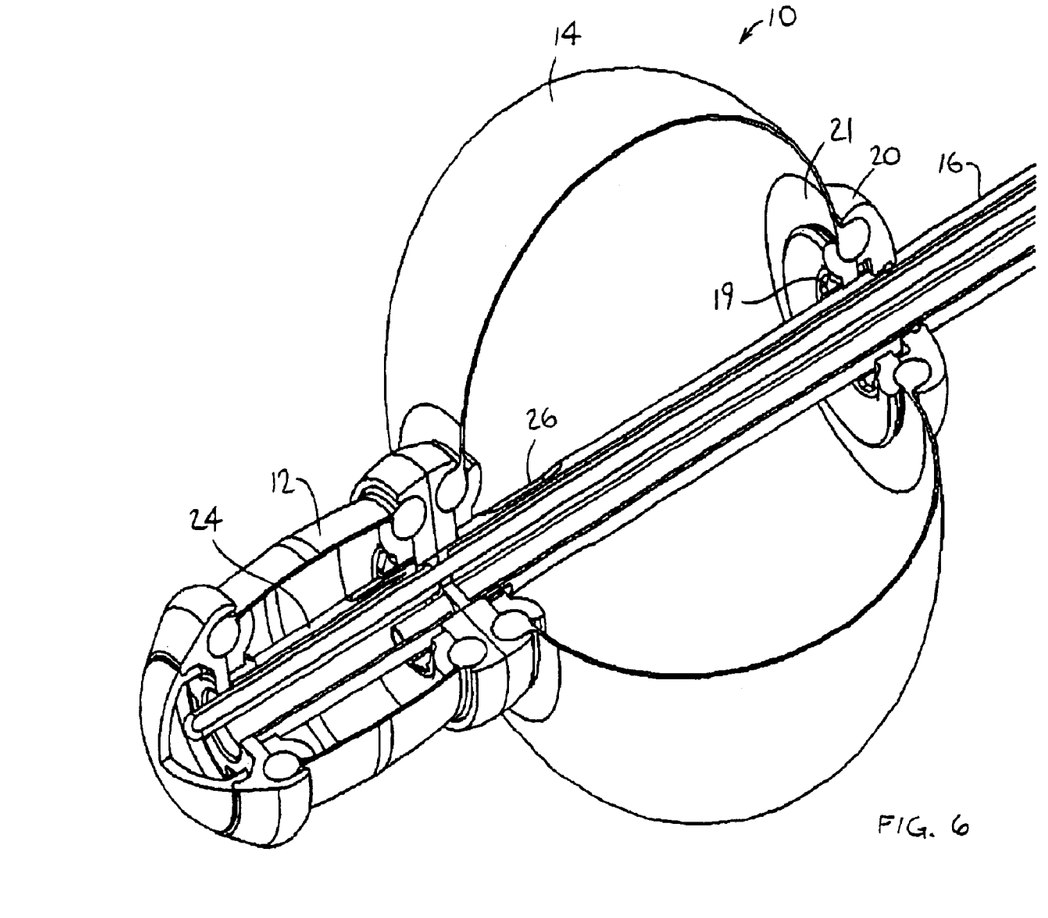
FIG. 6 is a simplified pictorial and cut-away illustration of the imaging system of FIG. 1A in the orientation of FIG. 4 or 5.

In FIG. 5, the proximal expandable element 14 continues to expand. Since the proximal expandable element 14 has already contacted the inner wall of body lumen 60, the continued expansion of expandable element 14 presses it against the inner wall of body lumen 60. The friction between expandable element 14 and the inner wall resists the radial expansion, with the result that most of the expansion of the proximal expandable element 14 is in the axial direction, as indicated by double arrow 57. This causes carrier tube 16 (along with imaging device 32) to advance distally in body lumen 60, as indicated by arrow 62, by a distance 6 in FIG. 5. The distal advancement of carrier tube 16 relative to guide member 50 may be detected by linear encoder 52 and decoder 54 (seen also in FIG. 1E).

Thus the expansion of second expandable element 14 may advance the carrier tube 16 distally in body lumen 60, without any need for sensing when second expandable element 14 has actually contacted the inner wall of body lumen 60. Rather once second expandable element 14 presses against the inner wall of body lumen 60, further expansion of second expandable element 14 may advance the carrier tube 16 distally in body lumen 60. The control system may control the further expansion of second expandable element 14 in order to control the amount of incremental advancement of carrier tube 16 and imaging device 32.

Figure 7:
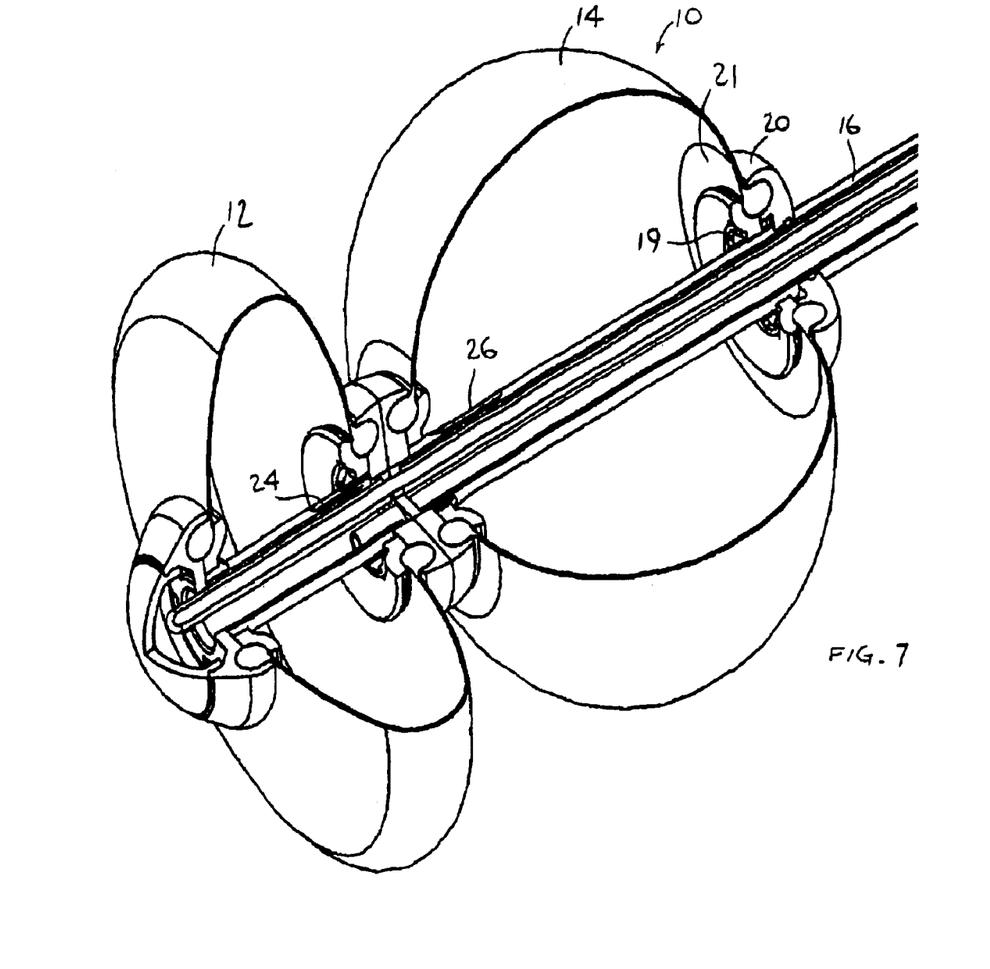
FIG. 7 is a simplified pictorial and cut-away illustration of the imaging system of FIG. 1A with the proximal expandable element expanded and a distal expandable element also expanded, in accordance with an embodiment of the present invention.
Figure 8:
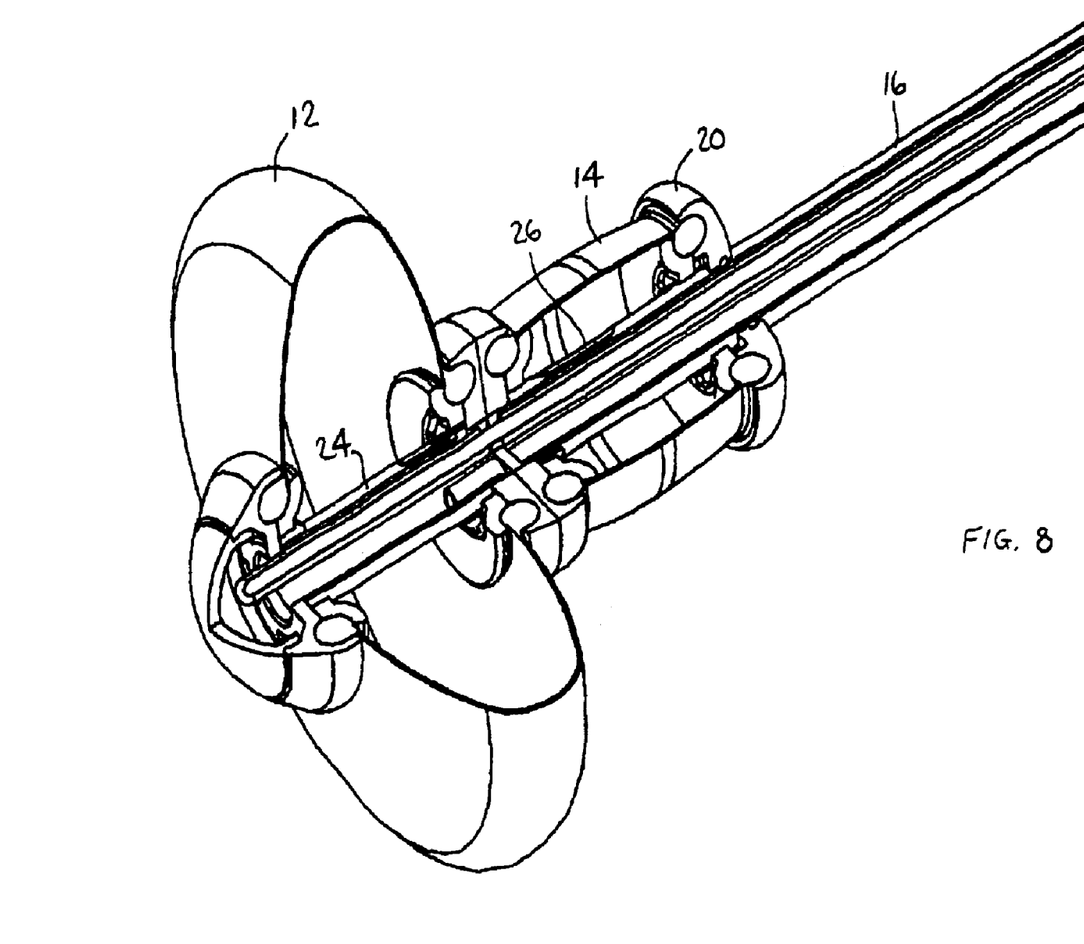
FIG. 8 is a simplified pictorial and cut-away illustration of the imaging system of FIG. 1A with the proximal expandable element contracted and the distal expandable element expanded, in accordance with an embodiment of the present invention.

In FIGS. 1F and 7, first (distal) expandable element 12 may be expanded radially. Both first and second expandable elements 12 and 14 now press against the inner wall of body lumen 60 (not shown in FIG. 7) and fix imaging system 10 in place in lumen 60. In FIGS. 1G and 8, second expandable element 14 may be contracted inwardly (e.g., deflated) so that it no longer presses against the inner wall of body lumen 60 (not shown in FIG. 8). Images may be captured by imaging device 32 at either of the orientations shown in FIGS. 7 and 8. As seen best in FIG. 1G, second expandable element 14 advances distally along carrier tube 16 when it is contracted inwardly, as indicated by arrow 67.

In order to advance carrier tube 16 further distally, first expandable element 12 may be contracted so that imaging system 10 returns to the contracted orientation of FIG. 2, and the operating cycle may be repeated to incrementally advance imaging system 10 through body lumen 60. The user or control system may ensure that carrier tube 16 does not move back proximally at each increment distal advance. Alternatively, as another way of ensuring that carrier tube 16 does not move back proximally at each incremental distal advance, first expandable element 12 may initially remain expanded against the inner wall of body lumen 60 while re-expanding second expandable element 14, and then first expandable element 12 may be contracted so as not to impede the incremental distal advancement caused by the re-expansion of second expandable element 14. The control system may control the timing of the contraction of the first expandable element 12 and the expansion of the second expandable element 14.

Imaging system 10 may be contracted to the orientation of FIG. 2 for removal from body lumen 60.

It will be appreciated by person skilled in the art that the present invention is not limited by what has been particularly shown and described herein above. Rather the scope of the present invention is defined only by the claims that follow:

What is claimed is:

1. An imaging system for imaging an inner wall of a lumen, the system comprising:
   an imaging device assembled on a carrier tube;
   a first outwardly expandable element mounted on said carrier tube, said first expandable element adapted, when expanded, to fix said carrier tube and said imaging device in place in said lumen; and
   a second outwardly expandable element mounted on said carrier tube, wherein said second expendable element is expandable both radially and axially,
   said imaging system comprising a mode of operation, wherein during expansion of said second expandable element, obstruction of the radial expansion of said second expandable element causes the axial expansion of said second expandable element to propel said carrier tube and said imaging device axially.

2. The imaging system according to claim 1, wherein said first expandable element is fixed axially to said carrier tube, and said second expandable element is slidable axially relative to said carrier tube.

3. The imaging system according to claim 1, wherein said carrier tube is formed with first and second apertures in fluid communication with said first and second expandable elements, respectively.

4. The imaging system according to claim 3, further comprising a first supply tube disposed in said carrier tube in fluid communication with said first aperture, and a second supply tube disposed in said carrier tube in fluid communication with said second aperture.

5. The imaging system according to claim 1, wherein said first and second expandable elements are expendable to different shapes.

6. The imaging system according to claim 1, wherein said first expandable element is expandable substantially radially with negligible axial expansion.

7. The imaging system according to claim 1, wherein said second expandable element is expandable generally spherically.

8. The imaging system according to claim 1, wherein said imaging device is mounted at a distal end of said carrier tube, distally of said first and second expandable elements.

9. The imaging system according to claim 1, further comprising a light source disposed in said carrier tube.

10. The imaging system according to claim 1, further comprising a suction tube disposed in said carrier tube.

11. The imaging system according to claim 1, further comprising a tool lumen-disposed in said carrier tube.

12. The imaging system according to claim 1, further comprising control wires disposed in said carrier tube.

13. The imaging system according to claim 1, further comprising a guide member disposed at a proximal end of said carrier tube.

14. The imaging system according to claim 1, further comprising a linear encoder disposed on said carrier tube, and a decoder operative to sense linear movement of said carrier tube with respect to said linear encoder.

15. The imaging system according to claim 1,
   wherein during expansion of said second expandable element, obstruction of the radial expansion of said second expandable element causes the axial expansion of said second expandable element to propel said carrier tube and said imaging device axially in a direction, and
   wherein said second expandable element is adapted to be contracted inwardly after said expansion thereof, and to advance in said direction along said carrier tube when said second expandable element is contracted inwardly.

16. The imaging system according to claim 1, wherein a proximal end of said second expandable element is slidingly sealed with respect to said carrier tube.

17. The imaging system according to claim 1,
wherein said first expandable element is mounted on said carrier tube distal to said second expandable element, and
wherein during said expansion of said second expandable element, said obstruction of the radial expansion of said second expandable element causes the axial expansion of said second expandable element to propel said carrier tube and said imaging device axially in a distal direction in said lumen.

18. The imaging system according to claim 1,
wherein said first expandable element is mounted on said carrier tube proximal to said second expandable element, and
wherein during said expansion of said second expandable element, said obstruction of the radial expansion of said second expandable element causes the axial expansion of said second expandable element to propel said carrier tube and said imaging device axially in a proximal direction in said lumen.

19. The imaging system according to claim 1, wherein during expansion of said second expandable element, obstruction of the radial expansion of said second expandable element by the inner wall of the lumen causes the axial expansion of said second expandable element to propel said carrier tube and said imaging device axially.

20. An imaging system for imaging an inner wall of a lumen, the system comprising:
an imaging device assembled on a carrier tube; and
a first outwardly expandable element and a second outwardly expandable element mounted on said carrier tube, wherein said second expandable element is expandable both radially and axially,
said imaging system comprising a mode of operation, wherein during expansion of said second expandable element, obstruction of the radial expansion of said second expandable element causes the axial expansion of said second expandable element to propel said carrier tube and said imaging device axially in a direction,
wherein said second expandable element is adapted to be contracted inwardly afire said expansion thereof, and to advance in said direction along said carrier tube when said second expandable element is contracted inwardly.

21. The imaging system according to claim 20, wherein said first expandable element is adapted, when expanded, to fix said carrier tube and said imaging device in place in said lumen.

22. The imaging system according to claim 20, wherein said first expandable element is fixed axially to said carrier tube, and said second expandable element is slidable axially relative to said carrier tube.

23. The imaging system according to claim 20, wherein said carrier tube is formed with first and second apertures in fluid communication with said first and second expandable elements, respectively.

24. The imaging system according to claim 23, further comprising a first supply tube disposed in said carrier tube in fluid communication with said first aperture, and a second supply tube disposed in said carrier tube in fluid communication with said second aperture.

25. The imaging system according to claim 20, wherein said first and second expandable elements are expandable to different shapes.

26. The imaging system according to claim 20, wherein said first expandable element is expandable substantially radially with negligible axial expansion.

27. The imaging system according to claim 20, wherein said second expandable element is expandable generally spherically.

28. The imaging system according to claim 20, further comprising a linear encoder disposed on said carrier tube, and a decoder operative to sense linear movement of said carrier tube with respect to said linear encoder.

29. The imaging system according to claim 20, wherein a proximal end of said second expandable element is slidingly sealed with respect to said carrier tube.

30. The imaging system according to claim 20,
wherein said first expandable element is mounted on said carrier tube distal to said second expandable element, and
wherein during said expansion of said second expandable element, said obstruction of the radial expansion of said second expandable element causes the axial expansion of said second expandable element to propel said carrier tube and said imaging device axially in a distal direction in said lumen.

31. The imaging system according to claim 20,
wherein said first expandable element is mounted on said carrier tube proximal to said second expandable element, and
wherein during said expansion of said second expandable element, said obstruction of the radial expansion of said second expandable element causes the axial expansion of said second expandable element to propel said carrier tube and said imaging device axially in a proximal direction in said lumen.

32. The imaging system according to claim 20, wherein during expansion of said second expandable element, obstruction of the radial expansion of said second expandable element by the inner wall of the lumen causes the axial expansion of said second expandable element to propel said carrier tube and said imaging device axially in the direction.

33. An imaging system for imaging an inner wall of a lumen by a user, the system comprising:
an imaging device assembled on a carrier tube; and
a first outwardly expandable element and a second outwardly expandable element mounted on said carrier tube, wherein at any given point in time a primary one of said expandable elements is expandable both radially and axially, and a secondary one of said expandable elements is expandable substantially radially with negligible axial expansion,
said imaging system comprising a mode of operation, wherein during expansion of said primary expandable element, obstruction of the radial expansion of said primary expandable element causes the axial expansion of said primary expandable element to propel said carrier tube and said imaging device axially.

34. The imaging system according to claim 33, wherein which of said first and second expandable elements is said primary expandable element and which is said secondary expandable element is selectable by said user while said imaging system is in said lumen.

35. The imaging system according to claim 33,
wherein, when said first expandable element is said primary expandable element, during expansion of said primary expandable element, obstruction of the radial expansion of said primary expandable element causes the axial expansion of said primary expandable element to propel said carrier tube and said imaging device axially in a first direction, and wherein, when said second expandable element is said primary expandable element, during expansion of said primary expandable element, obstruction of the radial expansion of said primary expandable element causes the axial expansion of said primary expandable element to propel said carrier tube and said imaging device axially in a second direction opposite said first direction.

36. The imaging system according to claim 33, wherein said secondary expandable element is fixed axially to said carrier tube, and said primary expandable element is slidable axially relative to said carrier tube.

37. The imaging system according to claim 33, wherein during expansion of said primary expandable element, obstruction of the radial expansion of said primary expandable element by the inner wall of the lumen causes the axial expansion of said primary expandable element to propel said carrier tube and said imaging device axially.

38. A method for imaging an inner wall of a lumen using an imaging device assembled on a carrier tube, said carrier tube having first and second outwardly expandable elements mounted thereon, the method comprising:

inserting said carrier tube into said lumen;

radially and axially expanding said second expandable element, such that obstruction of the radial expansion of said second expandable element causes the axial expansion of said second expandable element to propel said carrier tube and said imaging device axially; and expanding said first expandable element, so as to fix said carrier tube and said imaging device in place in said lumen.

39. The method according to claim 38, wherein expanding said first expandable element comprises axially fixing said first expandable element to said carrier tube, and wherein expanding said second expandable element comprises axially sliding said second expandable element relative to said carrier tube.

40. The method according to claim 39, wherein expanding said first expandable element comprises introducing a first fluid into said first expandable element via a first aperture formed in said carrier tube, and wherein expanding said second expandable element comprises introducing a second fluid into said second expandable element via a second aperture formed in said carrier tube.

41. The method according to claim 40, wherein introducing said first fluid comprises introducing said first fluid via a first supply tube disposed in said carrier tube in fluid communication with said first aperture, and wherein introducing said second fluid comprises introducing said second fluid via a second supply tube disposed in said carrier tube in fluid communication with said second aperture.

42. The method according to claim 38, wherein expanding said first and second expandable elements comprises expanding said first and second expandable elements to different shapes.

43. The method according to claim 38, wherein expanding said first expandable element comprises expanding said first expandable element substantially radially with negligible axial expansion.

44. The method according to claim 38, wherein expanding said second expandable element comprises expanding said second expandable element generally spherically.

45. The method according to claim 38, further comprising mounting said imaging device at a distal end of said carrier tube, distally of said first and second expandable elements.

46. The method according to claim 38, further comprising disposing a light source in said carrier tube.

47. The method according to claim 38, further comprising disposing a suction tube in said carrier tube.

48. The method according to claim 38, further comprising disposing a tool lumen in said carrier tube.

49. The method according to claim 38, further comprising disposing control wires in said carrier tube.

50. The method according to claim 38, further comprising disposing a guide member at a proximal end of said carrier tube.

51. The method according to claim 38, further comprising disposing a linear encoder on said carrier tube, and sensing linear movement of said carrier tube with respect to said linear encoder, using a decoder.

52. The method according to claim 38, wherein expanding such second expandable element comprises radially and axially expanding such second expandable element, such that obstruction of the radial expansion of said second expandable element causes the axial expansion of said second expandable element to propel said carrier tube and said imaging device axially in a direction, and comprising:

inwardly contracting said second expandable element after said expansion thereof; and advancing said second expandable element in said direction along said carrier tube when said second expandable element is contracted inwardly.

53. The method according to claim 38, further comprising slidingly sealing a proximal end of said second expandable element with respect to said carrier tube.

54. The method according to claim 38, wherein inserting said carrier tube comprises inserting said carrier tube into said lumen such that said first expandable element enters said lumen before said second expandable element enters said lumen, and wherein expanding such second expandable element comprises radially and axially expanding such second expandable element, such that obstruction of the radial expansion of said second expandable element causes the axial expansion of said second expandable element to propel said carrier tube and said imaging device axially in a distal direction in said lumen.

55. The method according to claim 38, wherein expanding such second expandable element comprises radially and axially expanding such second expandable element, such that obstruction of the radial expansion of said second expandable element causes the axial expansion of said second expandable element to propel said carrier tube and said imaging device axially in a proximal direction in said lumen.

56. The method according to claim 38, wherein radially and axially expanding said second expandable element comprises radially and axially expanding said second expandable element, such that obstruction of the radial expansion of said second expandable element by the inner wall of the lumen causes the axial expansion of said second expandable element to propel said carrier tube and said imaging device axially.

57. A method for imaging an inner wall of a lumen using an imaging device assembled on a carrier tube, said carrier tube having first and second outwardly expandable elements mounted thereon, the method comprising:

inserting said carrier tube into said lumen;

radially and axially expanding said second expandable element, such that obstruction of the radial expansion of said second expandable element causes the axial expansion of said second expandable element to propel said carrier tube and said imaging device axially in a direction;

expanding said first expandable element;

inwardly contracting said second expandable element after said expansion thereof; and advancing said second expandable element in said direction along said carrier tube when said second expandable element is contracted inwardly.

58. The method according to claim 57, wherein expanding said first expandable element comprises expanding said first expandable element so as to fix said carrier tube and said imaging device in place in said lumen.

59. The method according to claim 57, wherein expanding said first expandable element comprises axially fixing said first expandable element to said carrier tube, and wherein expanding said second expandable element comprises axially sliding said second expandable element relative to said carrier tube.

60. The method according to claim 57, wherein expanding said first expandable element comprises introducing a first fluid into said first expandable element via a first aperture formed in said carrier tube, and wherein expanding said second expandable element comprises introducing a second fluid into said second expandable element via a second aperture formed in said carrier tube.

61. The method according to claim 60, wherein introducing said first fluid comprises introducing said first fluid via a first supply tube disposed in said carrier tube in fluid communication with said first aperture, and wherein introducing said second fluid comprises introducing said second fluid via a second supply tube disposed in said carrier tube in fluid communication with said second aperture.

62. The method according to claim 57, wherein expanding said first and second expandable elements comprises expanding said first and second expandable elements to different shapes.

63. The method according to claim 57, wherein expanding said first expandable element comprises expanding said first expandable element substantially radially with negligible axial expansion.

64. The method according to claim 57, wherein expanding said second expandable element comprises expanding said second expandable element generally spherically.

65. The method according to claim 57, further comprising disposing a linear encoder on said carrier tube, and sensing linear movement of said carrier tube with respect to said linear encoder, using a decoder.

66. The method according to claim 57, further comprising slidingly sealing a proximal end of said second expandable element with respect to said carrier tube.

67. The method according to claim 57,
wherein inserting said carrier tube comprises inserting said carrier tube into said lumen such that said first expandable element enters said lumen before said second expandable element enters said lumen, and
wherein expanding such second expandable element comprises radially and axially expanding such second expandable element, such that obstruction of the radial expansion of said second expandable element causes the axial expansion of said second expandable element to propel said carrier tube and said imaging device axially in a distal direction in said lumen.

68. The method according to claim 57, wherein expanding such second expandable element comprises radially and axially expanding such second expandable element, such that obstruction of the radial expansion of said second expandable element causes the axial expansion of said second expandable element to propel said carrier tube and said imaging device axially in a proximal direction in said lumen.

69. The method according to claim 57, wherein radially and axially expanding said second expandable element comprises radially and axially expanding said second expandable element, such that obstruction of the radial expansion of said second expandable element by the inner wall of the lumen causes the axial expansion of said second expandable element to propel said carrier tube and said imaging device axially in the direction.

70. A method for imaging an inner wall of a lumen by a user using an imaging device assembled on a carrier tube, said carrier tube having first and second outwardly expandable elements mounted thereon, the method comprising:
inserting said carrier tube into said lumen;
selecting, at any given point in time, a primary one of said expandable elements to be expandable both radially and axially, and a secondary one of said expandable elements to be expandable substantially radially with negligible axial expansion; and
radially and axially expanding said primary expandable element, such that obstruction of the radial expansion of said primary expandable element causes the axial expansion of said primary expandable element to propel said carrier tube and said imaging device axially.

71. The method according to claim 70, wherein selecting comprises selecting by said user while said imaging system is in said lumen.

72. The method according to claim 70,
wherein, when said first expandable element has been selected to be said primary expandable element, during expansion of said primary expandable element, obstruction of the radial expansion of said primary expandable element causes the axial expansion of said primary expandable element to propel said carrier tube and said imaging device axially in a first direction, and
wherein, when said second expandable element has been selected to be said primary expandable element, during expansion of said primary expandable element, obstruction of the radial expansion of said primary expandable element causes the axial expansion of said primary expandable element to propel said carrier tube and said imaging device axially in a second direction opposite said first direction.

73. The method according to claim 70, wherein expanding said secondary expandable element comprises axially fixing said secondary expandable element to said carrier tube, and wherein expanding said primary expandable element comprises axially sliding said primary expandable element relative to said carrier tube.

74. The method according to claim 70, wherein radially and axially expanding said primary expandable element comprises radially and axially expanding said primary expandable element, such that obstruction of the radial expansion of said primary expandable element by the inner wall of the lumen causes the axial expansion of said primary expandable element to propel said carrier tube and said imaging device axially.

* * * * *